United States Patent [19]

Rettegi et al.

[11] 4,235,912
[45] Nov. 25, 1980

[54] BIOLOGICALLY ACTIVE NEW 8β-HYDRAZINOMETHYL-ERGOLINE DERIVATIVES AND A PROCESS FOR THE PREPARATION THEREOF

[75] Inventors: Tivadar Rettegi; Erzsébet Magó née Karácsony; Lajos Toldy; Jozsef Borsi; László Tardos, all of Budapest, Hungary

[73] Assignee: Richter Gedeon Vegyeszeti Gyar Rt, Budapest, Hungary

[21] Appl. No.: 21,947

[22] Filed: Mar. 19, 1979

[30] Foreign Application Priority Data

Mar. 20, 1978 [HU] Hungary .................... GO 1394

[51] Int. Cl.³ .................. C07D 457/02; A61K 31/48
[52] U.S. Cl. .................................... 424/261; 546/67
[58] Field of Search ................... 424/261; 546/67

[56] References Cited
FOREIGN PATENT DOCUMENTS 170271 3/1978 Hungary .

Primary Examiner—Mary C. Lee
Attorney, Agent, or Firm—Karl F. Ross

[57] ABSTRACT

The invention relates to new 8β-hydrazinomethyl-ergoline derivatives of the general formula (I),

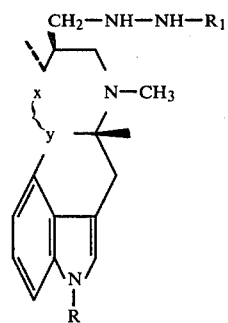

wherein
x y stands for a

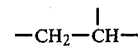

or

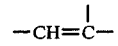

group,
R stands for hydrogen or methyl group, and
R₁ stands for hydrogen, a lower acyl group, a di-(loweralkylaminocarbonyl group, a group of the general formula

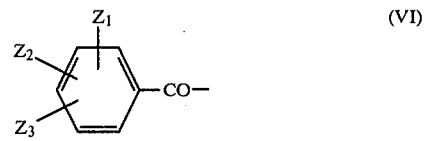

wherein $Z_1$, $Z_2$ and $Z_3$ each represent hydrogen, halogen or a trifluoromethyl group, or a group of the general formula (VII),

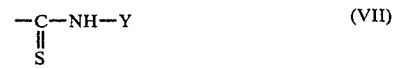

wherein Y represents a lower alkyl group, allyl group or phenyl group, and acid addition salts thereof. These compounds possess valuable antiserotonine, antidepressant and hypotensive effects, furthermore they can be applied as starting substances in the preparation of other biologically active ergoline derivatives.

The new compounds of the general formula (I) are prepared according to the invention by reacting the respective 6-methyl-8β-mesyloxymethyl or -tosyloxymethyl-ergoline derivatives with dry hydrazine. In order to obtain the N-substituted hydrazinomethyl compounds, the N-unsubstituted derivatives are reacted with an acylating agent or with an isothiocyanate.

8 Claims, No Drawings

BIOLOGICALLY ACTIVE NEW 8β-HYDRAZINOMETHYL-ERGOLINE DERIVATIVES AND A PROCESS FOR THE PREPARATION THEREOF

This invention relates to new 8β-hydrazinomethylergoline derivatives of the formula (I),

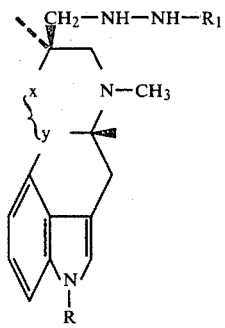

wherein
$\overset{\frown}{xy}$ is a

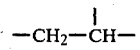

or

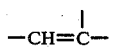

R is hydrogen or methyl, and
$R_1$ is hydrogen, lower acyl di-(lower)alkylaminocarbonyl a group of the formula

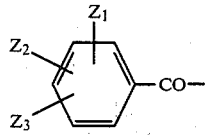

wherein $Z_1$, $Z_2$ and $Z_3$ each represent hydrogen, halogen or a trifluoromethyl group, or a group of the formula (VII),

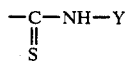

wherein Y represents lower alkyl group, allyl or phenyl,
and acid addition salts thereof. The invention also relates to pharmaceutical compositions containing these new compounds and a process for the preparation of the above new 8β-hydrazinomethyl-ergoline derivatives.

BACKGROUND OF THE INVENTION

In the last few years several semisynthetic compounds with ergolene or ergoline skeleton have been synthesized and introduced to therapy in addition to the natural ergot alkaloids (H. G. Floss: Tetrahedron 32, 873–912; 1976). Examples of these semisynthetic compounds are 1-methyllysergic acid butanolamide (Deseryl), lysergic acid butanolamide (Metegrin), 1,6-dimethyl-8β-carbobenzyloxy-aminomethyl-10α-ergoline (Metergoline), 1-methyl-10α-methoxy-dihydrolysergol-5'-bromo-nicotinate (Nicergoline), 6-methyl-8β-acetylaminomethyl-ergoline (Uterdina) and 2-chloro-6-methyl-8β-cyanomethyl-ergoline (Lergotril).

8β-Hydrazinomethyl-ergoline derivatives have not, to our knowledge been described so far in the literature.

DESCRIPTION OF THE INVENTION

Now it has been found that the new compounds of the formula (I) and their acid addition salts possess valuable therapeutic properties. These compounds can also be used as starting substances in the synthesis of other biologically active ergoline derivatives.

The new compounds of the formula (I) are prepared according to the invention as follows:

A compound of the formula (II),

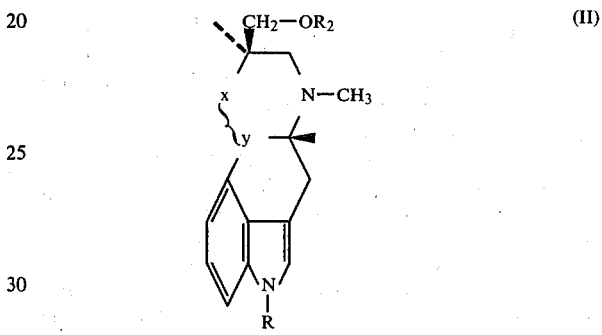

wherein $R_2$ is tosyl or mesyl is reacted with dry (anhydrous) hydrazine, and, if desired, (a) the resulting compound is reacted with an acyl halide of the formula (III),

wherein Q is lower alkyl di-(lower)-alkylamino or a group of the formula (VI), and in this latter formula $Z_1$, $Z_2$ and $Z_3$ are as defined above, or with an acid anhydride of the formula (IV),

wherein Q is as defined above, to obtain a compound of the general formula (I) wherein $R_1$ is lower acyl di-(lower)-alkylaminocarbonyl or of the formula (VI), or (b) the resulting compound is reacted with an isothiocyanate derivative of the formula (V),

wherein Y is lower alkyl, allyl or phenyl to obtain a compound of the formula (I), wherein $R_1$ is a group of the formula (VII).

If desired, the resulting compounds of the formula (I) are converted into their acid-addition salts by contacting them with a pharmaceutically acceptable acid.

According to a preferred method of the invention one proceeds as follows:

The starting substance of the formula (II) is suspended in dry hydrazine, the suspension is boiled for 30 minutes in a nitrogen atmosphere on an oil bath heated to 150° C., thereafter the separated crystals are filtered off and dried in vacuo. The resulting compound is dissolved in chloroform, a tertiary base is added, and the acyl chloride of the formula (III) is introduced into the mixture with cooling. The progress of the acylation is monitored by thin-layer chromatography (TLC). The resulting product can be purified by crystallization or by column chromatography. If desired, the product can be converted into its acid-addition salt. As salt-forming agent preferably maleic acid or hydrochloric acid is used.

According to another method the appropriate acid of the formula Q—COOH is reacted first with isobutyl chloroformate in the presence of N-methyl-morpholine, and the resulting mixed anhydride of the formula (IV) is reacted then with a dimethyl formamide solution of a compound of the formula (I), wherein $R_1$ is hydrogen.

The compounds of the formula (I), wherein $R_1$ is a group of the formula (VII), are prepared so that a compound of the formula (I), wherein $R_1$ is hydrogen, is dissolved in dry tetrahydrofuran, and the solution is treated with an isothiocyanate of the formula (V).

The compounds of the formula (II), used as starting substances in the process of the invention, can be prepared as described in the Hungarian Pat. No. 170,271.

As mentioned above, the new compounds according to the invention possess valuable therapeutic activity. The new compounds can antagonize the serotonine receptors, and exert antidepressant or hypotensive effect.

The antiserotonine effect of the new compounds was examined under in vitro and in vivo conditions. The in vitro tests were performed on isolated rat uterus sensitized with diethylstibestrol (see J. H. Gaddum; Brit. J. Pharmacol. 9, 240; 1954). The in vivo tests were performed according to the method of I. L. Bonta (Arch. Int. Pharmacodyn. 132, 147; 1961), by injecting 50 μg of serotonine into the plantar region of rats and measuring the oedema inhibiting effects of the compounds under examination. In these tests Methysergide (1-methyl lysergic acid butanolamide) was used as reference substance. The test results are summarized in Table 1.

TABLE 1

| Compound (Example No.) | Antiserotonine activity | | |
|---|---|---|---|
| | In vitro test $ED_{50}$ g/ml | In vivo tests $ED_{50}$ (50% inhibition of the oedema) mg/kg | |
| | | s.c. | p.o. |
| 4 | $10^{-6}$ to $10^{-9}$ | 0.3 | 3.0 |
| 6 | $10^{-6}$ to $10^{-9}$ | 0.05 | 3.0 |
| 7 | $10^{-6}$ to $10^{-9}$ | 0.03 | 3.0–10.0 |
| 8 | $10^{-9}$ | 0.160 | 3.0 |
| 9 | $10^{-9}$ | 0.055 | 0.780 |
| Methysergide | $5 \times 10^{-9}$ | 0.026 | 0.640 |

The data of Table 1 indicate that all of the compounds tested competitively block the smooth muscle contracting effect of serotonine on isolated organs, and exert this blocking effect in very small concentrations. Furthermore, the compounds strongly inhibit the serotonine-induced oedema upon both parenteral and oral administration. 6-Methyl-8β-[(N'-acetyl-hydrazino)-methyl]-ergol-9-ene. The compound prepared according to Example 9, proved to be outstandingly effective.

The new 8β-hydrazinomethyl-ergoline derivatives show antidepressant effects as tested on mice suffering from reserpine-induced depression. An intraperitoneal dosage of 5 mg/kg of reserpine was applied to induce depression. 18 hours later the body temperature of the animals was measured, 30 mg/kg of the compound under examination were administered intraperitoneally into the animals, and the body temperature of the animals was measured hourly for 5 hours. The maximum increase in temperature (i.e. the maximum body temperature measured after administering the compound minus the initial value) was considered as the measure of the antidepressant activity. In these tests Imipramine was used as a reference substance. The results are listed in Table 2.

TABLE 2

| Compound (Example No.) | Antidepressant activity Δt °C. |
|---|---|
| 1 | +2:8 |
| 5 | +1:5 |
| 6 | +2:5 |
| 7 | +2:4 |
| 8 | +1:6 |
| 14 | +7:8 |
| Imipramin [5-(3-dimethylamino-propyl)-10,11-dihydro-5H-dibenzo(b,f)azepin] | +5:0 |

6-Methyl-8β-([N'-methylthiocarbamoyl-hydrazino]-methyl)-ergol-9-ene, the compound prepared according to Example 14, proved to be outstandingly effective in the above test. The antidepressant activity of this compound is superior to that of Imipramine.

The hypotensive effect on anaesthetized animals in low dosages was tested on cats anaesthetized with an intraperitoneal dosage of 30 mg/kg of Pentothal. The arterial blood pressure was measured in the right carotid artery, and it was registered by a Hellige type polygraph. The compounds under examination were administered in an intravenous dosage of 0.5 mg/kg. Dihydroergotamine, used as a reference substance, was administered in an intravenous dosage of 2.0 mg/kg. The results of the tests are listed in Table 3.

TABLE 3

| Compound (Example No.) | Hypotensive activity | |
|---|---|---|
| | Decrease of blood pressure, mm Hg | Duration of the effect, hours |
| 6 | 20 to 30 | 0.5 to 1.0 |
| 14 | 50 to 60 | 1.0 to 1.5 |
| 8 | 50 to 70 | 2.0 to 3.0 |
| 9 | 20 to 40 | 1.0 to 2.0 |
| Dihydroergotamine | 30 to 40 | 1.0 to 1.5 |

As the table shows, some of the new compounds are superior to dihydroergotamine both in activity and with respect to the duration of the effect.

The new compounds of the formula (I) and their pharmaceutically acceptable acid-addition salts can be used in therapy directly or in the form of pharmaceutical compositions, such as tablets, coated tablets, capsules, suppositories, injectable solutions, etc., suitable for enteral or parenteral administration. Of the salts, the water-soluble ones are preferred. The pharmaceutical compositions are prepared by conventional methods, utilizing conventional inert, organic or mineral carriers (such as lactose, starch, talc, stearic acid, water, alcohols, natural and hardened oils, waxes, etc.) and/or auxiliary agents (such as preservatives, stabilizing agents, wetting agents, solubilizing aids, sweetening agents, dyestuffs, flavoring agents, etc.).

The invention is further elucidated with the aid of the following non-limiting Examples.

EXAMPLE 1

6-Methyl-8β-hydrazinomethyl-ergoline 5 g (0.0146 moles) of 6-methyl-8β-mesyloxymethyl-ergoline are suspended in 25 ml of dry hydrazine distilled from sodium hydroxide. The suspension is refluxed under a nitrogen atmosphere on an oil bath heated to 150° C. for 20 minutes after the complete dissolution of the solids. In this operation atmospheric moisture should be excluded carefully. The mixture is cooled and allowed to stand in a refrigerator. The separated crystals are filtered off, washed with water, and then dried in vacuo. 2.8 g (71%) of 6-methyl-8β-hydrazinomethyl-ergoline are obtained; m.p.: 171°–172° C., $[\alpha]_D^{20} = -62.8°$ (c=0.2, in tetrahydrofuran).

EXAMPLE 2

6-Methyl-8β-hydrazinomethyl-ergol-9-ene

One proceeds as described in Example 1 with the difference that 5 g of 6-methyl-8β-mesyloxymethyl-ergol-9-ene are used as a starting substance. 2.7 g (68%) of 6-methyl-8β-hydrazinomethyl-ergol-9-ene are obtained; m.p.: 162°–163° C., $[\alpha]_D^{20} = 0°$ (c=0.2, in tetrahydrofuran).

EXAMPLE 3

1,6-Dimethyl-8β-hydrazinomethyl-ergoline

The process is as described in Example 1 with the difference that 5.4 g of 1,6-dimethyl-8β-tosyloxymethyl-ergoline are used as starting substance. 2.2 g (56%) of 1,6-dimethyl-8β-hydrazinomethyl-ergoline are obtained; m.p.: 102°–103° C., $[\alpha]_D^{20} = -60.4°$ (c=0.2, in tetrahydrofuran).

EXAMPLE 4

6-Methyl-8β-([N'-acetyl-hydrazino]-methyl)-ergoline 0.6 g (0.0021 moles) of 6-methyl-8β-hydrazino-methyl-ergoline are introduced, under vigorous stirring, into a solution of 0.28 ml (0.0025 moles) of N-methyl-morpholine in 60 ml of dry chloroform. When the solid dissolves completely, a solution of 0.184 g (0.0023 moles) of acetyl chloride in 2 ml of acetonitrile is added dropwise, within 5 minutes, to the mixture. After the addition the pH of the mixture is checked, and when it is lower than 6, N-methyl-morpholine is introduced. The reaction mixture is stirred at room temperature for one hour, thereafter it is diluted with 30 ml of water, and the pH of the mixture is adjusted to 8 with aqueous ammonia. The mixture is shaken, the phases are separated from each other, the organic phase is washed twice with water, dried, and evaporated to dryness in vacuo. The dry residue is crystallized from ethanol. The separated crystals are filtered off, washed with a small amount of cold (5° C.) ethanol, and dried in vacuo. 0.5 g (72.4%) of 6-methyl-8β-([N'-acetyl-hydrazino]-methyl)-ergoline are obtained; m.p.: 213°–215° C., $[\alpha]_D^{20} = -38.7°$ (c=1, in 96% ethanol).

EXAMPLE 5

6-Methyl-8β-[(N'-{4'-fluorobenzoyl}-hydrazino)-methyl]-ergoline hydrogenmaleate The process is carried out as described in Example 4 with the difference that 1.1 g (0.0039 moles) of 6-methyl-8β-hydrazinomethyl-ergoline and 0.68 g (0.0047 moles) of 4-fluorobenzoyl chloride are used as the starting substances. The resulting base is treated with an alcoholic solution of maleic acid to form the salt. 0.7 g (45.6%) of 6-methyl-8β-[(N'-{4'-fluorobenzoyl}-hydrazino)-methyl]ergoline hydrogenmaleate are obtained; m.p.: 215°–217° C., $[\alpha]_D^{20} = -27.5°$ (c=1, in 96% ethanol).

EXAMPLE 6

6-Methyl-8β-([N'-dimethylcarbamoyl-hydrazino]-methyl)-ergoline

The process is carried out as in Example 4 with the difference that 0.6 g (0.00213 moles) of 6-methyl-8β-hydrazinomethyl-ergoline and 0.25 g (0.00234 moles) of dimethylcarbamoyl chloride are used as the starting substances. 0.5 g (69%) of 6-methyl-8β-([N'-dimethylcarbamoyl-hydrazino]-methyl)-ergoline are obtained; m.p.: 205°–206° C., $[\alpha]_D^{20} = -36.2°$ (c=1, in 96% ethanol).

EXAMPLE 7

1,6-Dimethyl-8β-([N'-acetyl-hydrazino]-methyl)-ergoline 0.6 g of acetic acid are dissolved in 25 ml of acetonitrile with stirring. The solution is cooled to −15° C., and 1.39 ml of isobutyl chloroformate and 1.1 ml of N-methyl-morpholine are added. After 5 minutes of stirring a solution of 2.8 g of 1,6-dimethyl-8β-hydrazinomethyl-ergoline in 10 ml of acetonitrile is added to the mixture. The mixture is slowly (within 30 minutes) warmed to room temperature, stirred at room temperature for 2 hours, then evaporated in vacuo. The residue is dissolved in 200 ml of chloroform, and 100 ml of water are added. The pH of the aqueous phase is adjusted to 8 with 10% aqueous ammonia, and the mixture is shaken. The organic phase is separated, and the aqueous phase is extracted thrice with 100 ml of chloroform. The chloroform fractions are combined and evaporated to dryness in vacuo. The residue is subjected to column chromatography in order to remove the occasional impurities. 60 g of silica gel are used as adsorbent, and the column is eluted with a 30:0.3:9 mixture of chloroform, water and methanol. The effluent is analyzed by thin layer chromatography. The fractions containing a substance with an $R_f$ value of 0.75 are combined, evaporated in vacuo, and the residue is crystallized from alcohol. 1.9 g (60.4%) of 1,6-dimethyl-8β-[(N'-acetyl-hydrazino)-methyl]-ergoline are obtained; m.p.: 190°–192° C., $[\alpha]_D^{20} = -29.7°$ (c=1, in 96% ethanol).

EXAMPLE 8

6-Methyl-8β-([N'-dimethylcarbamoyl-hydrazino]-methyl)-ergol-9-ene

The process is carried out as described in Example 4 with the difference that 1.2 g (0.0043 moles) of 6-methyl-8β-hydrazinomethyl-ergol-9-ene and 0.51 g (0.0047 moles) of dimethylcarbamoyl chloride are used as starting substances. 0.75 g (49.5%) of 6-methyl-8β-([N'- dimethylcarbamoyl-hydrazine]-methyl)-ergol-9-ene are obtained; m.p.: 185°–187° C.

EXAMPLE 9

6-Methyl-8β-([N'-acetyl-hydrazino]-methyl)-ergol-9-ene

The process is carried out as in Example 7 with the difference that 1.2 g (0.0043 moles) of 6-methyl-8β-hydrazinomethyl-ergol-9-ene and 0.25 ml of acetic acid are used as starting substances, and the chromatographic purification is omitted. The dry residue obtained after evaporating the chloroform solution is crystallized from alcohol. 0.6 g (43.4%) of 6-methyl-8β-([N'-acetyl-hydroazino]-methyl)-ergol-9-ene are obtained; m.p. 158°–160° C., $[\alpha]_D^{20} = +116°$ (c=1, in 96% ethanol).

EXAMPLE 10

6-Methyl-8β-[(N'-{3'-trifluoromethyl-benzoyl}-hydrazino)-methyl]-ergol-9-ene hydrogenmaleate The process is carried out as described in Example 4 with the difference that 1.5 g (0.0054 moles) of 6-methyl-8β-hydrazinomethyl-ergol-9-ene and 1.13 g (0.0059 moles) of 3-trifluoromethyl-benzoyl fluoride are used as starting substances. The resluting base is treated with an alcoholic solution of maleic acid to form the salt. 1.3 g (53%) of 6-methyl-8β-[(N'-{3'-trifluoromethyl-benzoyl}-hydrazino)-methyl]-ergol-9-enehydrogenmaleate are obtained; m.p.: 159°–160° C., $[\alpha]_D^{20} = +81°$ (c=1, in 96% ethanol).

EXAMPLE 11

6-Methyl-8β-([N'-methylthiocarbamoyl-hydrazino]-methyl)-ergoline 1.2 g (0.0043 moles) of 6-methyl-8β-hydrazinomethyl-ergoline are dissolved in 120 ml of dry tetrahydrofuran, the solution is cooled to 0.5° C., and 0.38 g (0.0052 moles) of methyl isothiocyanate are added with stirring. The reaction mixture is stirred for one hour, and the solvent is distilled off in vacuo. The residue is subjected to chromatography on a column packed with 40 g of silica gel; a 100:0.3:20 mixture of chloroform, water and methanol is applied as eluting agent. The eluents which contain a single compound with an $R_f$ value of 0.45 are combined and evaporated, and the dry residue is crystallized from ethanol. 1.1 g (76.8%) of 6-methyl-8β-([N'-methylthiocarbamoyl-hydrazino]-methyl)-ergoline are obtained; m.p.: 220°–221° C., $[\alpha]_D^{20} = -45.7°$ (c=1, in 96% ethanol).

EXAMPLE 12

6-Methyl-8β-([N'-phenylthiocarbamoyl-hydrazino]-methyl)-ergoline

The process is carried out as described in Example 11 with the difference that 0.7 g (0.0025 moles) of 6-methyl-8β-hydrazinomethyl-ergoline and 0.38 g (0.0028 moles) of phenyl isocyanate are applied as the starting substances. The fractions containing a single substance with an $R_f$ value of 0.60 are combined and evaporated, and the dry residue is crystallized from ethanol. 0.85 g (81.5%) of 6-methyl-8β-([N'-phenylthiocarbamoyl-hydrazino]-methyl)-ergoline are obtained; m.p.: 205°–206° C., $[\alpha]_D^{20} = -54.5°$ (c=1, in 96% ethanol).

EXAMPLE 13

6-Methyl-8β-([N'-allylthiocarbamoyl-hydrazino]-methyl)-ergoline

The process is carried out as in Example 11 with the difference that 4 g (0.142 moles) of 6-methyl-8β-hydrazino-methyl-ergoline and 1.68 g (0.0170 moles) of allyl isothiocyanate are used as starting substances. The fractions containing a single substance with an $R_f$ value of 0.70 are combined and evaporated, and the dry residue is crystallized from alcohol. 3.8 g (72.6%) of 6-methyl-8β-([N'-allylthiocarbamoyl-hydrazino]-methyl)-ergoline are obtained; m.p.: 207°–208° C., $[\alpha]_D^{20} = -53.2°$ (c=1, in 96% ethanol).

EXAMPLE 14

6-Methyl-8β-([N'-methylthiocarbamoyl-hydrazino]-methyl)-ergol-9-ene

The process is carried out as described in Example 11 with the difference that 1.0 g (0.0036 moles) of 6-methyl-8β-hydrazino-methyl-ergol-9-ene and 0.31 g (0.0043 moles) of methyl isothiocyanate are used as starting substances. 0.9 g (70.7%) of 6-methyl-8β-([N'-methylthiocarbamoyl-hydrazino]-methyl)-ergol-9-ene are obtained; m.p.: 218°–220° C.

EXAMPLE 15

Preparation of a pharmaceutical composition

Oral tablets containing 1 mg. of active agent can be prepared for therapeutical purposes from the following components:

| | | |
|---|---:|---|
| 6-methyl-8β-[(N'-methyl-thiocarbamoyl-hydrazino)-methyl]-ergolene | 1 | mg. |
| milk sugar | 246.5 | mg. |
| corn starch | 25 | mg. |
| polyvinyl pyrrolidone | 10 | mg. |
| talcum | 15 | mg. |
| magnesium stearate | 2.5 | mg |
| average weight | 300.0 | mg. |

The tablets are provided with a film or sugar coating.

What we claim is:

1. An 8β-hydrazinomethyl-ergoline compound of the formula (I),

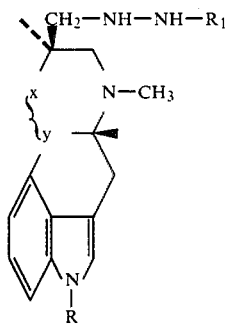

wherein
$\overset{\frown}{x\ y}$ is

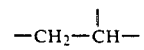

or $$-CH=\overset{|}{C}-$$

R is hydrogen or methyl, and
R₁ is hydrogen, lower alkylcarbonyl, a di-(lower)-alkylaminocarbonyl, a group of the formula (VI), $$\begin{matrix} Z_1 \\ Z_2 \\ Z_3 \end{matrix} \diagdown CO-$$

wherein
Z₁, Z₂ and Z₃ each represent hydrogen, halogen or trifluoromethyl,
or a group of the formula (VII), $$-\underset{\underset{S}{\|}}{C}-NH-Y \qquad (VII)$$

wherein
Y is lower alkyl, allyl or phenyl,
or an acid-addition salt thereof.

2. 6-Methyl-8β-[(N'-acetylhydrazino)-methyl]-ergol-9-ene or a pharmaceutically acceptable acid-addition salt thereof.

3. 6-Methyl-8β-[(N'-methylthiocarbamoyl-hydrazino)-methyl]-ergol-9-ene or a pharmaceutically acceptable acid-addition salt thereof.

4. The compound defined in claim 1 selected from the group consisting of:
  (1) 6-methyl-8beta-hydrazinomethyl-ergoline;
  (2) 6-methyl-8beta-hydrazinomethyl-ergol-9-ene;
  (3) 1,6-dimethyl-8beta-hydrazinomethyl-ergoline;
  (4) 6-methyl-8beta-[(N'-acetyl-hydrazino)-methyl]-ergoline;
  (5) 6-methyl-8beta [(N'-[4'-fluorobenzoyl]-hydrazino)-methyl]-ergoline;
  (6) 6-methyl-8beta-[(N'-dimethylcarbamoyl-hydrazino)-methyl]-ergoline;
  (7) 1,6-dimethyl-8beta-[(N'-acetyl-hydrazino)-methyl]-ergoline;
  (8) 6-methyl-8beta-[(N'-dimethylcarbamoyl-hydrazino)-methyl]-ergol-9-ene;
  (9) 6-methyl-8beta-[(N'-acetyl-hydrazino)-methyl]ergol-9-ene;
  (10) 6-methyl-8beta-[(N'-[3'-trifluoromethyl-benzoyl]-hydrazino)-methyl]-ergol-9-ene;
  (11) 6-methyl-8beta-[(N'-methylthiocarbamoyl-hydrazino)-methyl]-ergoline;
  (12) 6-methyl-8beta-[(N'-phenylthiocarbamoyl-hydrazino)-methyl]-ergoline;
  (13) 6-methyl-8beta-[(N'-allylthiocarbamoyl-hydrazino)-methyl]-ergoline; and
  (14) 6-methyl-8beta-[(N'-methylthiocarbamoyl-hydrazino]-methyl]-ergol-9-ene;
or a pharmaceutically acceptable acid addition salt thereof.

5. An antiserotonine antidepressant or hypotensive composition containing as active ingredient a compound as defined in claim 1, or a pharmaceutically acceptable acid addition salt thereof, together with a conventional pharmaceutical carrier and/or auxiliary agent.

6. A process for the preparation of an 8beta-hydrazino-methyl-ergoline derivative of the formula (I), wherein
$\overset{\frown}{x\,y}$ is $$-CH_2-\overset{|}{CH}-$$

or $$-CH=\overset{|}{C}-,$$

R is hydrogen or methyl, and
R₁ is hydrogen, lower alkylcarbonyl, di-(lower)-alkylaminocarbonyl, a group of the formula (VI), $$\begin{matrix} Z_1 \\ Z_2 \\ Z_3 \end{matrix} \diagdown CO-$$

wherein
Z₁, Z₂ and Z₃ each represent hydrogen, halogen or a trifluoromethyl,
or a group of the formula (VII)

$$-\underset{\underset{S}{\|}}{C}-NH-Y$$

wherein
Y is lower alkyl, allyl or phenyl, or an acid-addition salt thereof, which comprises the step
(a) of reacting a compound of the formula (II),

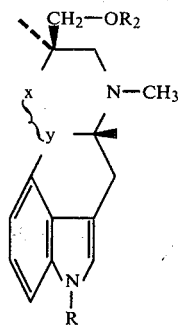

wherein $R_2$ is tosyl or mesyl, with dry hydrazine to yield the desired product wherein $R_1$ is hydrogen;

and in the case where $R_1$ is lower alkylcarbonyl, di-(lower)-alkylaminocarbonyl, or a group of the formula (VI)

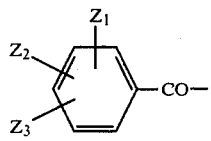

(b) reacting the product formed during step (a) with an acyl halide of the Formula (III)

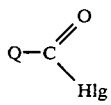

wherein
Hlg is halogen; and

Q is lower alkyl, di-(lower)-alkyl-amino, a group of the formula (IV)

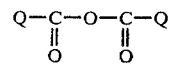

or a group of the formula (VI)

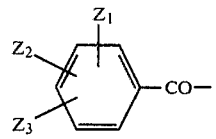

to obtain the desired product; and
in the case where $R_1$ is a group of the formula (VII)

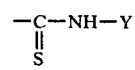

($b_1$) reacting the compound formed during step (a) with an isothiocyanate of the formula (V)

to yield the desired product.

7. The process defined in claim 6 wherein the product produced during step (a), step (b) or step ($b_1$) is converted to a pharmaceutically acceptable acid addition salt.

8. A method of treating an animal subject to effect antiserotonine, antidepressant or hypotensive therapy which comprises administering an effective amount of a compound as defined in claim 1 or a pharmaceutically effective acid-addition salt thereof.

* * * * *